United States Patent
Inokuchi et al.

(10) Patent No.: US 9,421,156 B2
(45) Date of Patent: *Aug. 23, 2016

(54) SILICONE ELASTOMER PARTICLE AND AN AQUEOUS DISPERSION COMPRISING THE SAME

(71) Applicant: SHIN-ETSU CHEMICAL CO., LTD., Tokyo (JP)

(72) Inventors: Yoshinori Inokuchi, Annaka (JP); Ryuji Horiguchi, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/263,462

(22) Filed: Apr. 28, 2014

(65) Prior Publication Data

US 2014/0335044 A1  Nov. 13, 2014

(30) Foreign Application Priority Data

May 9, 2013  (JP) .................................. 2013-99556

(51) Int. Cl.
| | |
|---|---|
| A61K 8/891 | (2006.01) |
| A61K 8/49 | (2006.01) |
| A61Q 1/00 | (2006.01) |
| C08K 5/1545 | (2006.01) |
| C08G 77/50 | (2006.01) |
| A61K 8/34 | (2006.01) |
| A61Q 1/02 | (2006.01) |
| A61K 8/67 | (2006.01) |
| A61K 8/895 | (2006.01) |
| A61K 8/02 | (2006.01) |
| C08G 77/12 | (2006.01) |
| C08G 77/20 | (2006.01) |

(52) U.S. Cl.
CPC ................ *A61K 8/498* (2013.01); *A61K 8/025* (2013.01); *A61K 8/347* (2013.01); *A61K 8/4926* (2013.01); *A61K 8/678* (2013.01); *A61K 8/891* (2013.01); *A61K 8/895* (2013.01); *A61Q 1/00* (2013.01); *A61Q 1/02* (2013.01); *C08G 77/50* (2013.01); *C08K 5/1545* (2013.01); *A61K 2800/522* (2013.01); *A61K 2800/57* (2013.01); *A61K 2800/654* (2013.01); *C08G 77/12* (2013.01); *C08G 77/20* (2013.01)

(58) Field of Classification Search
CPC ....... A61K 8/891; A01N 25/04; C08G 77/12; C08G 77/20
USPC ................................. 528/32, 31, 20
See application file for complete search history.

(56) References Cited

U.S. PATENT DOCUMENTS

| | | | |
|---|---|---|---|
| 2006/0094610 A1 * | 5/2006 | Yamato et al. | ................ 510/130 |
| 2010/0158824 A1 | 6/2010 | Lin | |
| 2012/0251598 A1 | 10/2012 | Ikeda et al. | |

FOREIGN PATENT DOCUMENTS

| | | |
|---|---|---|
| JP | A-11-217444 | 8/1999 |
| WO | 2011 136394 | * 11/2011 |

OTHER PUBLICATIONS

Nov. 18, 2014 Search Report issued in European Application No. 14 16 7548.
Nov. 13, 2015 Office Action issued in U.S. Appl. No. 14/824,428.
May 9, 2016 Office Action issued in U.S. Appl. No. 14/824,428.

* cited by examiner

Primary Examiner — Kuo-Liang Peng
(74) Attorney, Agent, or Firm — Oliff PLC

(57) ABSTRACT

One of the purposes of the present invention is to provide a silicone elastomer particle and an aqueous dispersion of the silicone elastomer particles, which prevent generation of odor from oxygenation of nonionic surfactants. The present invention provides a silicone elastomer particle having a crosslinking structure formed by an addition reaction of a monovalent aliphatic unsaturated group bonded to a silicon atom and a hydrogen atom bonded to another silicon atom, wherein the silicone elastomer particle contains an antioxidant. Further, present invention provides an aqueous dispersion comprising the silicone elastomer particles, a nonionic surfactant and water.

12 Claims, No Drawings

SILICONE ELASTOMER PARTICLE AND AN AQUEOUS DISPERSION COMPRISING THE SAME

CROSS REFERENCE

This application claims the benefits of Japanese Patent application No. 2013-099556 filed on May 9, 2013, the contents of which are incorporated by reference.

The present invention relates to a silicone elastomer particle and an aqueous dispersion comprising the same.

BACKGROUND OF THE INVENTION

Silicone elastomer particles and aqueous dispersions of silicone elastomers have been used for a purpose of providing a smooth or soft feeling to cosmetics. Silicone elastomer particles scatter light and, therefore, makeup cosmetics, such as foundations, containing the silicone elastomer particles, provide natural finish without artificial gloss.

Usually, silicone elastomer particles used for cosmetics have a crosslinking structure formed by an addition reaction of vinylsilyl groups and hydrosilyl groups in the presence of a platinum group metal catalyst. Spherical particles or dispersions of the particles is prepared in a method comprising steps of emulsifying a liquid silicone mixture comprising a silicone having vinylsilyl groups and a silicone having hydrosilyl groups in water with a nonionic surfactant and, then, subjected to an addition reaction in the presence of a platinum group metal catalyst to cause crosslinking. There is a problem such that at the time of the reaction or over time, the polyether moiety of the nonionic surfactant is oxygenated by an effect of the platinum group metal catalyst to cause odor. Japanese Patent Application Laid-Open No. Hei-11-217444 describes the method where a compound which decreases the catalyst activity of a platinum group catalyst is contained in silicone rubber particles obtianed as mentioned above.

PRIOR LITERATURE

Patent Literature

[Paten Literature 1] Japanese Patent Application Laid-Open No. Hei-11-217444

SUMMARY OF THE INVENTION

However, the compound described in the aforesaid Patent Literature 1, which decreases the catalyst activity of a platinum group catalyst, is an amino compound or a silicone containing an amino group and there is concern that these compounds irritate skin. Therefore, persons hesitate to use the silicone rubber particles described in the aforesaid Patent Literature 1 for cosmetics, such as base cosmetics, makeup cosmetics and sunscreen cosmetics, which are applied on skin to form a coat kept on the skin for a long time.

One of the purposes of the present invention is to provide a silicone elastomer particle and an aqueous dispersion of the silicone elastomer particles, which prevent generation of odor due to oxygenation of nonionic surfactants.

The present inventors have made research and found that a silicone elastomer particle containing a compound which prevents oxygenation of nonionic surfactants attains the afore-mentioned purpose.

Thus, the present invention provides a silicone elastomer particle having a crosslinking structure formed by an addition reaction of a monovalent aliphatic unsaturated group bonded to a silicon atom and a hydrogen atom bonded to another silicon atom, wherein the silicone elastomer particle contains an antioxidant. Further, present invention provides an aqueous dispersion comprising the silicone elastomer particle, a nonionic surfactant and water.

Further, the present invention provides a method for preparing the silicone elastomer particle and a method for preparing the aqueous dispersion.

The present invention is characterized in that the silicone elastomer particle contains an antioxidant. That is, in the aqueous dispersion containing a silicone elastomer particle and a nonionic surfactant, an antioxidant is presence in the silicone elastomer particle, but not in water. In a silicone elastomer particle having a nonionic surfactant on its surface, an antioxidant is presence in the silicone elastomer particle, but not on its surface. As will be described below, it is noted that the antioxidant may be presence further on the surface of the silicone elastomer particle, in water of the aqueous dispersion or in the nonionic surfactant. On account of these, when the present silicone elastomer particle or aqueous dispersion containing the particle is added to cosmetics, an amount of the antioxidant which acts on a nonionic surfactant present on or near the surface of the silicone elastomer particle is not decreased and generation of odor is efficiently prevented.

As stated above, the present silicone elastomer particle and aqueous dispersion containing the silicone elastomer particle prevent oxygenation of a nonionic surfactant and, therefore, are added to cosmetics to prevent generation of odor over time. Further, when the present silicone elastomer particles are added to cosmetics containing a nonionic surfactant, it is expected that generation of odor over time is also prevented. Further, the present silicone elastomer particle and aqueous dispersion does not cause irritation to skin. Therefore, the present silicone elastomer particle and aqueous dispersion are suitable for use in cosmetics.

DETAILED DESCRIPTION OF THE INVENTION

The present invention will be described below in detail.

[Silicone Elastomer Particle]

The shape of the silicone elastomer particle is not limited, but preferably spherical shape. The term "spherical shape" means not only that the particle is of exact sphere, but also that the particle may be of a deformed sphere whose aspect ratio, i.e. ratio of a longest diameter to a shortest diameter, is usually, on average, 1 to 4, preferably 1 to 2, more preferably 1 to 1.6, further preferably 1 to 1.4. As described below, in the case where a silicone elastomer particle is prepared by emulsifying and dispersing a liquid silicone in water with a surfactant and, then, curing the liquid silicone, a shape of the particle obtained is spherical. The shape of the silicone elastomer particle can be confirmed by observation with an electron microscope. In the case of the aqueous dispersion containing the silicone elastomer particles whose particle diameter is approximately 1 μm or more, the shape of the silicone elastomer particle can be confirmed by observation with an optical microscope without removing water. In the other case where the particle diameter of the particle in the aqueous dispersion is less than 1 μm, water is removed and, then, the shape of the silicone elastomer particle can be confirmed by observation with an electron microscope.

The silicone elastomer particle preferably has a volume-average particle diameter of 0.1 to 100 μm, more preferably 0.2 to 40 μm, but not limited to particular one. If the volume-average particle is less than the aforesaid lower limit, a smooth feeling and a light scattering effect cannot be provided sufficiently to cosmetics. If the volume-average particle diameter is larger than the aforesaid upper limit, smooth feeling of cosmetics decreases, rough feeling appears, and a light scattering effect decreases. A method for determining a volume-average particle diameter is selected depending on a particle diameter of the silicone composite particle. When the particle diameter is 1 μm or more, an electric resistance method is used. When the particle diameter is less than 1 μm, a laser diffraction-scattering method is used.

The silicone elastomer particle is preferably non-sticky and has a rubber hardness of 5 to 90, more preferably 10 to 80, as determined with a Type A durometer in accordance with the Japanese Industrial Standards (JIS) K 6253. If the rubber hardness is less than the aforesaid lower limit, a smooth feeling of cosmetics decreases. If the rubber hardness is larger than the aforesaid upper limit, the soft feeling of cosmetics tends to decrease.

The silicone elastomer particle is preferably a cured product having a linear organosiloxane block represented by the formula —$(R^1_2SiO_{2/2})_n$—, wherein $R^1$ is a substituted or unsubstituted monovalent hydrocarbon group having 1 to 30 carbon atoms and n is a integer of from 5 to 5,000.

Examples of $R^1$ include alkyl groups such as a methyl group, an ethyl group, a propyl group, a butyl group, a pentyl group, a hexyl group, a heptyl group, an octyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a docosyl group, a tricosyl group, a tetracyl group, and a triacontyl group; aryl groups such as a phenyl group, a tolyl group, and a naphthyl group; aralkyl groups such as a benzyl group and a phenethyl group; alkenyl groups such as a vinyl group and an allyl group; cycloalkyl groups such as a cyclopentyl group, a cyclohexyl group, and a cycloheptyl group; and those hydrocarbon groups wherein a part or all of the hydrogen atoms bonded to a carbon atom of these groups are substituted with a substituent such as halogen atoms such as a fluorine atom, a chlorine atom, a bromine atom and an iodine atom and/or with an acryloyloxy group, a methacryloyloxy group, an epoxy group, a glycidoxy group and a carboxyl group.

The silicone rubber particle is obtained by curing a curable liquid silicone and has a cross-linking structure, i.e. three dimension network structure. A method of curing a curable liquid silicone to obtain a silicone elastomer particle may be any conventional method. For instance, an organo(poly)siloxane having monovalent olefinically unsaturated groups each bonded to a silicon atom such as a vinyl silyl group ($\equiv$SiCH=CH$_2$) is addition reacted with an organo(poly)siloxane having hydrogen atoms each bonded to a silicon atom, i.e. hydrosilyl group ($\equiv$SiH).

A silicone elastomer particle can be prepared by an addition reaction of a liquid silicone mixture comprising an organo(poly)siloxane which is represented by an average formula: $R^2_aR^3_bSiO_{(4-a-b)/2}$ and has at least two monovalent olefinically unsaturated groups per molecule and an organohydrogen(poly)siloxane which is represented by an average formula: $R^4_cH_dSiO_{(4-c-d)/2}$ and has at least three hydrogen atoms each bonded to a silicone atom, hereinafter referred to as SiH group, per molecule. A silicone elastomer particle can also be prepared by an addition reaction of a liquid silicone mixture comprising an organo(poly)siloxane which is represented by an average formula: $R^2_aR^3_bSiO_{(4-a-b)/2}$ and has at least three monovalent olefinically unsaturated groups per molecule and an organohydrogen(poly)siloxane which is represented by an average formula: $R^4_cH_dSiO_{(4-c-d)/2}$ and has at least two SiH groups per molecule. Amounts of the organo(poly)siloxane having monovalent olefinically unsaturated groups and the organohydrogen(poly)siloxane is such that the number of the SiH group is 0.5 to 2, per the number of the monovalent olefinically unsaturated group.

In the aforesaid formula, $R^2$ is a substituted or unsubstituted monovalent hydrocarbon group having 1 to carbon atoms except aliphatic unsaturated groups. $R^3$ is a monovalent olefinically unsaturated group having 2 to 6 carbon atoms. "a" and "b" are positive numbers satisfying the (in)equations, $0<a<3$, $0<b<=3$ and $0.1<=a+b<=3$, preferably $0<a<=2.295$, $0.005<=b<=2.3$ and $0.5<=a+b<=2.3$. $R^4$ is a substituted or unsubstituted monovalent hydrocarbon group having 1 to 30 carbon atoms except aliphatic unsaturated groups. "c" and "d" are positive numbers satisfying the (in)equations, $0<c<3$, $0<d<=3$ and $0.1<=c+d<=3$, preferably $0<c<=2.295$, $0.005<=d<=2.3$ and $0.5<=c+d<=2.3$.

Examples of $R^2$ include an alkyl group such as a methyl group, an ethyl group, a propyl group, a butyl group, a pentyl group, a hexyl group, a heptyl group, an octyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a docosyl group, a tricosyl group, a tetracyl group and a triacontyl group; an aryl group such as a phenyl group, a tolyl group and a naphthyl group; an aralkyl group such as a benzyl group and a phenethyl group; a cycloalkyl group such as a cyclopentyl group, a cyclohexyl group and a cycloheptyl group; and those hydrocarbon groups wherein a part or all of the hydrogen atoms bonded to a carbon atom of these groups is substituted with a substituent such as a halogen atom such as a fluorine atom, a chlorine atom, a bromine atom and an iodine atom and/or an acryloyloxy group, a methacryloyloxy group, an epoxy group, a glycidoxy group and a carboxyl group. Particularly, it is industrially preferable that 50 mole % or more of $R^2$ is a methyl group.

Examples of $R^3$ include a vinyl group, an allyl group, a propenyl group, a butenyl group, a pentenyl group and a hexenyl group. Particularly, a vinyl group is industrially preferable.

Examples of $R^4$ include the same groups as those described for $R^2$ above.

The organo(poly)siloxane and the organohydrogen(poly)siloxane preferably have a dynamic viscosity at 25 degrees C. of 100,000 mm$^2$/s or less, more preferably 10,000 mm$^2$/s or less. If the dynamic viscosity is higher than the aforesaid upper limit, it is difficult to obtain particles having a narrow molecular weight range in the present method described below. The organo(poly)siloxane and the organohydrogen(poly)siloxane may have a linear, cyclic or branched structure. Particularly, a linear structure is preferable. The dynamic viscosity in the present invention is determined with an Ostwald viscometer.

In the aforesaid liquid silicone mixture, at least three monovalent aliphatic unsaturated groups are present in the organo(poly)siloxane and/or at least three hydrogen atoms are present in the organohydrogen(poly)siloxane. Otherwise, a cured rubber tends to be sticky.

The platinum group metal catalyst may be any well-known or known catalyst for hydrosilylation. Examples of the catalyst include an element of platinum group metals such as platinum, including platinum black, rhodium and palladium; platinum chloride such as H$_2$PtCl$_4$.kH$_2$O, H$_2$PtCl$_6$.kH$_2$O, NaHPtCl$_6$.kH$_2$O, KHPtCl$_6$.kH$_2$O, Na$_2$PtCl$_6$.kH$_2$O, K$_2$PtCl$_4$.kH$_2$O, PtCl$_4$.kH$_2$O, PtCl$_2$, and Na$_2$HPtCl$_4$.kH$_2$O, wherein "k" is an integer of 0 to 6, preferably 0 or 6; a chloroplatinic acid and a chloroplatinate;

an alcohol-modified chloroplatinic acid (see U.S. Pat. No. 3,220,972); a complex of chloroplatinic acid with an olefin (see U.S. Pat. Nos. 3,159,601, 3,159,662, and 3,775,452); a platinum group metal, such as platinum black and palladium, supported on a carrier such as alumina, silica and carbon; a rhodium-olefin complex; chlorotris(triphenylphosphine) rhodium (Wilkinson catalyst); and a complex of platinum chloride, chloroplatinic acid or chloroplatinate with siloxane having a vinyl group, in particular vinyl group-containing cyclic siloxane.

The amount of the platinum group metal catalyst may be an effective amount to promote a hydrosilylation. If the amount of the catalyst is too large, oxygenation of a polyether moiety of the nonionic surfactant is not prevented and odor tends to occur. The amount of the catalyst is usually such that the amount of the platinum group metal in the catalyst is about 0.1 to about 100 ppm by mass, preferably about 0.5 to about 50 ppm by mass, more preferably about 1 to about 30 ppm by mass, relative to a total mass of the liquid silicone mixture.

The present silicone elastomer particle is characterized in that it contains an antioxidant. The antioxidant acts directly on the nonionic surfactant to prevent oxygenation of the nonionic surfactant. In particular, the silicone elastomer particle obtained in the aforesaid hydrosilation contains the platinum group metal catalyst and, therefore, the polyether moiety of the nonionic surfactant tends to be oxidized. The present silicone elastomer particle prevents the oxygenation of the polyether moiety of the nonionic surfactant and thereby prevents generation of odor over time. In particular, the antioxidant is contained in the silicone elastomer particle and, therefore, when the silicone elastomer particle or the aqueous dispersion containing the silicone elastomer particles is added to cosmetics, an amount of the antioxidant which acts on nonionic surfactants presence on or near the surface of the silicone elastomer particle is not decreased, so that oxygenation of the nonionic surfactant is effectively prevented. In contrast, if an water-soluble antioxidant is added to an aqueous dispersion of silicone elastomer particles, which is then added to an aqueous cosmetic, the antioxidant is diluted, an amount of the antioxidant which acts on nonionic surfactants present on or near the surface of the silicone elastomer particle decreases, so that oxygenation of the nonionic surfactant cannot be prevented sufficiently.

In the present invention, the antioxidant is preferably soluble in a liquid silicone, so that the antioxidant is smoothly incorporated in the silicone elastomer particle. Further, in particular, the antioxidant is preferably insoluble in water. On account of the insolubility in water, the antioxidant is effectively incorporated in the silicone elastomer particle in the present preparation method. If the antioxidant is soluble in water, not an entire amount of the antioxidants is incorporated in the silicone elastomer particle to lower the effect.

Any antioxidant which can prevent oxygenation of a nonionic surfactant may be used. In particular, antioxidants which are permitted to use as raw materials for cosmetics are preferable, such as, for instance, tocopherol, p-t-butylphenol, butylhydroxyanisol, dibutylhydroxytoluene, pentaerythritol tetrakis(3,5-di-tert-butyl-4-hydroxyhydrocinnamate) and ethoxyquin.

The present silicone elastomer particle may have a nonionic surfactant on its surface. Further, the present silicone elastomer particle may contain a nonionic surfactant.

As mentioned above, the antioxidant contained in the present silicone elastomer particle acts directly on a nonionic surfactant and prevents oxygenation of the nonionic surfactant. An amount of the antioxidant to be contained in the silicone elastomer particle is an effective amount so as to prevent oxygenation of the nonionic surfactant present on and/or in the particle, and/or in an aqueous dispersion (see below) and/or a cosmetic. In particular, the amount of the antioxidant to be contained in the silicone elastomer particle is preferably 10 to 2,000 ppm, further preferably 50 to 1,000 ppm based on the silicone elastomer particle. Alternatively, the amount of the antioxidant may be set to be 1 to 200 times, more preferably 5 to 100 times, as much in mass as the platinum group metal in a platinum group metal catalyst contained in the silicone elastomer particle.

The present silicone elastomer particle may further contain a silicone oil, an organosilane, inorganic powder and an organic powder. Amounts of those may be determined according to conventional silicone elastomer particles.

[Aqueous Dispersion of the Silicone Elastomer Particles]

The present invention further provides an aqueous dispersion comprising the afore-mentioned silicone elastomer particles, a nonionic surfactant and water. The nonionic surfactant works as an emulsifier for a liquid silicone, and further as a dispersant for the silicone elastomer particles to provide an aqueous dispersion.

Examples of the nonionic surfactant include a polyoxyethylene alkyl ether, a polyoxyethylene polyoxypropylene alkyl ether, a polyoxyethylene alkyl phenyl ether, a polyethylene glycol fatty acid ester, a polyoxyethylene sorbitan fatty acid ester, a polyoxyethylene sorbit fatty acid ester, a polyoxyethylene glycerin fatty acid ester, a polyglycerin fatty acid ester, a propylene glycol fatty acid ester, a polyoxyethylene castor oil, a polyoxyethylene cured castor oil, a polyoxyethylene cured castor oil fatty acid ester, a polyoxyethylene alkyl amine, a polyoxyethylene fatty acid amide, an organopolysiloxane modified with polyoxyethylene, and an organopolysiloxane modified with polyoxyethylene polyoxypropylene.

These nonionic surfactants may be used singly or as a mixture of two or more. When two or more nonionic surfactants are used, a nonionic surfactant having no polyether moiety, such as a sorbitan fatty acid ester and a glycerin fatty acid ester may be combined.

An amount of the silicone elastomer particles in the aqueous dispersion is preferably 5 to 80 mass %, further preferably 10 to 60 mass %, relative to a total mass of the aqueous dispersion. If the amount of the silicone elastomer particles is less than the aforesaid lower limit, an amount of the silicone elastomer particle relative to an amount of the aqueous dispersion decreases, a larger amount of the aqueous dispersion needs to be added to cosmetics and, thereby the production of the cosmetics becomes inefficient. If the amount of the silicone elastomer is larger than the aforesaid upper limit, viscosity of the aqueous dispersion is too high, so that handling is difficult.

An amount of the nonionic surfactant in the aqueous dispersion is preferably 0.01 to 15 mass %, further preferably 0.05 to 10 mass %, relative to a total mass of the aqueous dispersion. If the amount of the nonionic surfactant is less than the aforesaid lower limit, it is difficult to emulsify the liquid silicones. Meanwhile, even if the amount of the nonionic surfactant is larger than the upper limit, a particle diameter of silicone elastomer particles does not become smaller, dispersibility of silicone elastomer particles is not improved and, rather, generation of odor due to oxygenation of the nonionic surfactant tends to increase.

The aqueous dispersion of the silicone elastomer particles may contain surfactants other than the nonionic surfactant, such as anionic surfactants, cationic surfactants and amphoteric surfactants, in order to improve the dispersibility of the particles.

Examples of the anionic surfactant include alkyl sulfate ester salt, polyoxyethylene alkylether sulfate ester salt, polyoxyethylene alkylphenyl ether sulfate ester salt, sulfate ester salt of aliphatic acid alkylol amide, alkyl benzene sulfur acid salt, polyoxyethylene alkylphenyl ether sulfur acid salt, alpha-olefin sulfur acid salt, alpha-sulfo aliphatic acid ester salt, alkylnaphthalene sulfur acid salt, alkyldiphenylether disulfur acid salt, alkane sulfur acid, N-acyl taurine acid salt, dialkylsulfosuccinic acid salt, monoalkylsulfosuccinic acid salt, polyoxyethylene alkyl ether sulfosuccinic acid salt, aliphatic acid salt, polyoxyethylene alkyl ether carboxylic acid salt, N-acylamino acid salt, monoalkyl phosphoric acid ester salt, dialkyl phosphoric acid ester salt and polyoxyethylene alkylether phosphoric acid ester salt.

Examples of the cationic surfactant include an alkyl trimethyl ammonium salt, a dialkyl dimethyl ammonium salt, a polyoxyethylene alkyl dimethyl ammonium salt, a dipolyoxyethylene alkyl methyl ammonium salt, a tripolyoxyethylene alkyl ammonium salt, an alkyl benzyl dimethyl ammonium salt, an alkyl pyridinium salt, a monoalkyl amine salt and a monoalkylamide amine salt.

Examples of the amphoteric surfactant include an alkyl dimethyl amine oxide, an alkyl dimethyl carboxybetaine, an alkylamide propyl dimethyl carboxybetaine, an alkyl hydroxysulfobetaine and an alkyl carboxymethyl hydroxyethyl imidazolinium betaine.

The aqueous dispersion of the silicone elastomer particle may contain a water-soluble polymer in order to increase the dispersibility of the particle. Examples of the water-soluble polymer include a nonionic water-soluble polymer, an anionic water-soluble polymer, a cationic water-soluble polymer and an amphoteric water-soluble polymer, but are not limited to these.

Examples of the nonionic water-soluble polymer include a copolymer of vinylalcohol and vinyl acetate, a polymer of acrylamide, a polymer of vinyl pyrrolidone, a copolymer of vinyl pyrrolidone and vinyl acetate, polyethyleneglycol, a polymer of isopropylacrylamide, a polymer of methyl vinyl ether, starch, methyl cellulose, hydroxyethyl cellulose, hydroxypropyl cellulose, guar gum and xanthan gum.

Examples of the anionic water-soluble polymer include a polymer of sodium acrylate, a copolymer of sodium acrylate and sodium maleate, a copolymer of sodium acrylate and acrylamide, a polymer of styrenesulfonic acid sodium, a copolymer of polyisoprene surfonic acid sodium and styrene, a polymer of sodium naphthalenesulfonate, carboxymethylstarch, starch phosphate, carboxymethyl cellulose, sodium alginate, gum arabic, carrageenan, sodium chondroitin sulfate and sodium hyaluronate.

Example of the cationic water-soluble polymer include a polymer of dimethyl diallyl ammonium chloride, a polymer of vinyl imidazoline, a polymer of methyl vinyl imidazolium chloride, a polymer of ethyl acrylate trimethyl ammonium chloride, a polymer of ethyl methacrylate trimethyl ammonium chloride, a polymer of (3-acrylamidopropyl)trimethylammonium chloride, a polymer of (3-methacrylamidepropyl)trimethylammonium chloride, a copolymer of epichlorohydrin and dimethylamine, a polymer of ethylene imine, a quaternary compound of polyethylene imine, a polymer of allylamine hydrochloride salt, polylysine, cationic starch, cationic cellulose, chitosan, and these substances copolymerized with a monomer containing a nonionic group or an anionic group.

Examples of the amphoteric water-soluble polymer include a copolymer of ethyl acrylate trimethyl ammonium chloride, acrylic acid and acrylamide; a copolymer of ethyl methacrylate trimethyl ammonium chloride, acrylic acid and acrylamide; and Hofmann degradation product of a polymer of acrylamide.

The aforesaid aqueous dispersion may further contain an antiseptic agent and an antibacterial agent. Examples of the antiseptic agent include paraoxybenzoate alkylester, benzoic acid, sodium benzoate, sorbic acid, potassium sorbate and phenoxyethanol. Examples of the antibacterial agent include benzoic acid, salicylic acid, phenol, sorbic acid, paraoxybenzoate alkylester, parachloro metacresol, hexachlorophene, benzalkonium chloride, chlorhexidine chloride, triclorocarbanilide, photosensitizer and phenoxyethanol.

[Method for Preparing the Silicone Elastomer Particle and the Aqueous Dispersion]

The present invention further provides a method for preparing the silicone elastomer particle and the aqueous dispersion. (i) One of the methods for incorporating the antioxidant in the silicone elastomer particle comprises steps of dispersing or dissolving a liquid silicone-soluble antioxidant in the liquid silicones in advance and, then, curing the liquid silicones to obtain silicone elastomer particles containing the antioxidant. (ii) Another method comprises steps of adding an antioxidant to an emulsion of the liquid silicones, stirring them to dissolve the antioxidant in the liquid silicones and, then, curing the liquid silicones to obtain a silicone elastomer particle containing the antioxidant. The antioxidant used in this method needs to be soluble in the liquid silicones and insoluble in water. (iii) Further, the other method comprises steps of adding an antioxidant to an aqueous dispersion of the silicone elastomer particles, stirring them to thereby have the antioxidant contained in the silicone elastomer particles. The antioxidant used in this method also needs to be soluble in the liquid silicones and insoluble in water.

In the aforesaid methods, on account of the insolubility in water of the antioxidant, the antioxidant remains hardly in the aqueous phase of the aqueous dispersion or on the surface of the silicone elastomer particle. Almost the whole amount of the antioxidant added is incorporated in the silicone elastomer particle. Even if part of the antioxidant remains in aqueous phase of the dispersion or on the surface of the silicone elastomer particle, the aqueous dispersion or the silicone elastomer particle may be used as it is. The antioxidant may be dissolved in a solvent and added. When the dispersibility of the antioxidant in water is poor, the antioxidant may be dissolved in a surfactant and added to the emulsion. In particular, it is convenient and preferable that the antioxidant is dispersed or dissolved in the liquid silicone mixture in advance.

The first embodiment of the present method comprises steps of dissolving an antioxidant in a liquid silicone mixture comprising an organo(poly)siloxane having at least two monovalent aliphatic unsaturated groups each bonded to each one silicon atom and an organohydrogen(poly)siloxane having at least two hydrogen atoms each bonded to each one silicon atom, provided that the at least three monovalent aliphatic unsaturated groups and/or the at least three hydrogen atom are present in each one molecule; subsequently adding water and a nonionic surfactant thereto, stirring and emulsifying them, and curing said mixture in the presence of a platinum group metal catalyst to obtain a silicone elastomer particle.

The second embodiment of the present method comprises steps of stirring water, a nonionic surfactant and a liquid silicone mixture comprising an organo(poly)siloxane having at least two monovalent aliphatic unsaturated groups each bonded to each one silicon atom and an organohydrogen (poly)siloxane having at least two hydrogen atoms each bonded to each one silicon atom, provided that the at least three monovalent aliphatic unsaturated groups and/or the at least three hydrogen atom are present in each one molecule to emulsify them; subsequently adding an antioxidant, which is soluble to said liquid silicone mixture and insoluble in water with stirring; and, then, curing said mixture in the presence of a platinum group metal catalyst to obtain a silicone elastomer particle.

The third embodiment of the present method comprises steps of adding an antioxidant which is soluble in a liquid silicone and insoluble in water to an aqueous dispersion comprising a nonionic surfactant, water and a silicone elastomer particle having a crosslinking structure formed by an addition reaction of a monovalent aliphatic unsaturated groups each bonded to a silicon atom and hydrogen atoms each bonded to another silicon atom and, then, stirring them to thereby have said antioxidant contained in said silicone elastomer particle. In this method, the silicone elastomer particle may be prepared in conventional manners.

Where the silicone elastomer particle contains a silicone oil, an organosilane, inorganic powder or organic powder, these may be added to the liquid silicone mixture in advance.

The emulsification may be conducted with a conventional emulsification and dispersion apparatus. Examples of the emulsification and dispersion apparatus include a high-speed rotation and centrifugal dispersion type agitator such as a homodisper; a high-speed rotation and shearing type agitator such as a homomixer; a high-pressure injection-type emulsification disperser such as a homogenizer; a colloid mill; and an ultrasonic emulsifier.

The platinum group metal catalyst may be those described above. The platinum group metal catalyst may be added to an emulsion of the liquid silicone mixture or dissolved in the liquid silicone mixture in advance, as mentioned above. In the former case, the platinum group metal catalyst may be dissolved in a solvent and added. When the dispersibility of the catalyst in water is poor, it is preferable that the catalyst is dissolved in a surfactant and added to the emulsion. The surfactant may be those as described above. In particular, the nonionic surfactant is preferable. In the case where the platinum group metal catalyst is dissolved in the liquid silicone mixture in advance, it is better to cool the mixture to a low temperature such as 5 degrees C. or below so as to prevent curing until finishing the step of the emulsification. The addition curing reaction may be conducted at room temperature. If the reaction is not complete, the curing may be conducted under heating at a temperature below 100 degrees C.

The present silicone elastomer particle is prepared by removing water from the aqueous dispersion obtained in the afore-mentioned methods. Water may be removed by volatilization or evaporation with heating under normal pressure or reduced pressure, whereby the nonionic surfactant which is non-volatile remains and adheres on the surface of the silicone elastomer particle. The nonionic surfactant is contained sometimes in the silicone particle obtained. The silicone elastomer particle having the nonionic surfactant on its surface may be used after removing the nonionic surfactant. Specifically, water is removed by, for instance, heating the dispersion being standing, heating the dispersion being stirred as fluid, spraying and dispersing the dispersion in hot air stream in a spray dryer, or using a fluid heating medium. As a pre-treatment before the afore-mentioned step, the dispersion may be concentrated by, for instance, centrifugalization or decantation. A salt or an alcohol may be added to the dispersion to break the dispersion state and, then, the resulting materials are be concentrated by filtration, centrifugalization or decantation.

EXAMPLES

The present invention will be explained below in further detail with reference to a series of the Examples and the Comparative Examples, though the present invention is in no way limited by these Examples. In the following descriptions, dynamic viscosity is determined at 25 degrees C. with an Ostwald viscometer, and percentage, "%", in concentrations and contents, is by mass.

Example 1

Aqueous Dispersion of Silicone Elastomer Particles (i) In a one-liter glass beaker, put were 457 g of methyl vinyl polysiloxane which is represented by the following formula (1):

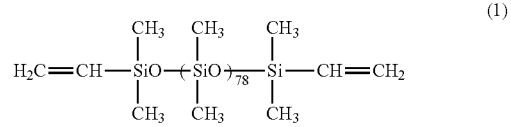

and has a dynamic viscosity of 130 mm$^2$/s; 43 g of methyl hydrogen polysiloxane which is represented by the following formula (2):

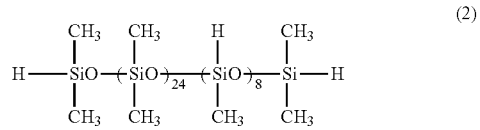

and has a dynamic viscosity of 30 mm$^2$/s, wherein this amount of the methyl hydrogen polysiloxane gives the number of the hydrosilyl groups of 1.17, per olefinically unsaturated group of the methyl vinyl polysiloxane; and 0.10 g of tocopherol, and stirred with a homomixer at 2,000 rpm to dissolve each other.

(ii) Subsequently, 6 g of polyoxyethylene lauryl ether having 9 units derived from ethylene oxide, and 40 g of water were added and, then, stirred with a homomixer at 8,000 rpm, whereby an oil-in-water state was obtained and thickening was observed. Then, the stirring was continued for further 15 minutes. Subsequently, 497 g of water was added thereto with stirring at 2,000 rpm to obtain a homogenous white emulsion. This emulsion was taken in a one-liter glass flask equipped with a stirrer having anchor type stirring blades, and the temperature was adjusted to 15-20 degrees C., to which then added with stirring was a solution consisting of 0.8 g of a solution of chloroplatinic acid-olefin complex in isododecane, containing 0.5 mass % of platinum, and 1 g of polyoxyethylene lauryl ether having 9 units derived from ethylene oxide. The resulting mixture was stirred for 12 hours at the same temperature. Subsequently, 43 g of polyoxyethylene lauryl ether having 9 units derived from ethylene oxide, 5 g of sodium benzoate and 1 g of citric acid were added to the resulting mixture and stirred for 10 minutes at the same temperature to obtain an aqueous dispersion.

In the aforesaid step (i), the entire amount of tocopherol was dissolved in the silicone mixture and, therefore, the silicone elastomer particles in the aqueous dispersion obtained in the step (ii) contained the entire amount of tocopherol added in the step (i).

The shape of the silicone elastomer particles in the aqueous dispersion thus obtained was spherical under observation with an optical microscope and the volume-average particle diameter thereof was 3 μm, as determined with a particle size distribution measurement instrument using an electric resistance method, Multisizer 3, manufactured by Beckman Coulter, Inc.

Rubber hardness of the silicone elastomer particle contained in the aqueous dispersion was determined according to the following method.

The methyl vinyl polysiloxane represented by the afore-mentioned formula (1), the methyl hydrogen polysiloxane represented by the afore-mentioned formula (2), tocopherol and the solution of chloroplatinic acid-olefin complex in isododecane, containing 0.5 mass % of platinum, were mixed in the afore-mentioned ratio, poured into an aluminum petri dish up to a depth of 10 mm and allowed to stand at 25 degrees C. for 24 hours. Then, the mixture was heated in a thermostat at 50 degrees C. for one hour to obtain a silicone elastomer containing tocopherol. Rubber hardness of the silicone elastomer was 43, as determined with a durometer A hardness meter.

The aqueous dispersion obtained in the aforesaid step (ii) was transferred to a one-liter plastic bottle and allowed to stand for one day and, then, a sensory test on odor was conducted. No odor was sensed.

Example 2

Silicone Elastomer Particles (i) In a one-liter glass beaker, put were 500 g of methyl vinyl polysiloxane which is represented by the following formula (3):

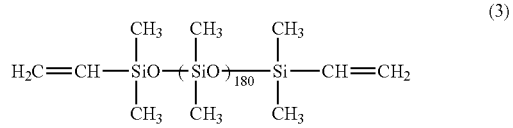

and has a dynamic viscosity of 600 mm²/s;
2 g of a methyl hydrogen polysiloxane which is represented by the aforesaid formula (2) and has a dynamic viscosity of 30 mm²/s, wherein this amount of the methyl hydrogen polysiloxane gives the number of the hydrosilyl groups of 1.13, per olefinically unsaturated group of the methyl vinyl polysiloxane; and 0.10 g of tocopherol, and stirred with a homomixer at 2,000 rpm to be dissolved each other.

(ii) Subsequently, 1.2 g of polyoxyethylene lauryl ether having 9 units derived from ethylene oxide, and 100 g of water were added and, then, stirred with a homomixer at 8,000 rpm, whereby an oil-in-water state was obtained and thickening was observed. Then, the stirring was continued for further 15 minutes. Subsequently, 396 g of water was added with stirring at 2,000 rpm to obtain a homogenous white emulsion. This emulsion was taken in a one-liter glass flask equipped with a stirrer having anchor type stirring blades, and the temperature was adjusted to 20-25 degrees C., to which then, added with stirring was a solution consisting of 0.8 g of a solution of chloroplatinic acid-olefin complex in isododecane, containing 0.5 mass % of platinum, and 1 g of polyoxyethylene lauryl ether having 9 units derived from ethylene oxide. The resulting mixture was stirred for 12 hours at the same temperature to obtain an aqueous dispersion.

In the aforesaid step (i), the entire amount of tocophelol was dissolved in the silicone mixture and, therefore, the silicone elastomer particles in the aqueous dispersion obtained in the step (ii) contained the entire amount of tocophelol added in the step (i).

The shape of the silicone elastomer particles in the aqueous dispersion thus obtained was spherical under observation with an optical microscope and the volume-average particle diameter thereof was 12 μm, as determined with a particle size distribution measurement instrument using an electric resistance method, Multisizer 3, manufactured by Beckman Coulter, Inc.

The water was removed from the aqueous dispersion by volatilization with a spray dryer, manufactured by Nihon Buchi Co., Ltd., Type: B-290, and conditions: an inlet temperature of 150 degrees C., an exit temperature of about 80 degrees C. and a feeding rate of the aqueous dispersion of 200 g/hr, to obtain silicone elastomer particles containing tocopherol. The polyoxyethylene lauryl ether used is non-volatile and, therefore, the entire amount of the polyoxyethylene lauryl ether used in the aforesaid process adheres on the surface of the silicone elastomer particles. The shape of the silicone elastomer particles thus obtained was spherical under observation with an electron microscope.

Rubber hardness of the silicone elastomer particle was determined according to the following method.

The methyl vinyl polysiloxane represented by the afore-mentioned formula (3), the methyl hydrogen polysiloxane represented by the afore-mentioned formula (2), tocopherol and the solution of chloroplatinic acid-olefin complex in isododecane, containing 0.5 mass % of platinum, were mixed in the afore-mentioned ratio, poured into an aluminum petri dish up to a depth of 10 mm and allowed to stand at 25 degrees C. for 24 hours. Then, the mixture was heated in a thermostat at 50 degrees C. for one hour to obtain a silicone elastomer containing tocopherol. Rubber hardness of the silicone elastomer was 28, as determined with a durometer A hardness meter.

The silicone elastomer particles obtained in the aforesaid step (ii) were transferred to a two-liter plastic bottle and allowed to stand for one day and, then, a sensory test on odor was conducted. No odor was sensed. Further, the silicone elastomer particles were stored at normal room temperature for one month and, then, a sensory test on odor was conducted. No odor was sensed.

Example 3

Foundation

A foundation was prepared, consisting of the aqueous dispersion obtained in Example 1 and the following components in amounts as described below.

| | (Components) | Weights, g |
|---|---|---|
| 1. | Decamethylcyclopentasiloxane | 225.0 |
| 2. | Dimethylpolysiloxane, viscosity: 6 mm²/s | 75.0 |
| 3. | Polyether-modified silicone[1] | 17.5 |

-continued

| | (Components) | Weights, g |
|---|---|---|
| 4. | Octadecyl dimethyl benzyl ammonium-modified montmorillonite | 7.5 |
| 5. | Iron oxide treated with an amino acid, N-acyl glutamate. | 12.5 |
| 6. | Titanium oxide treated with triethoxysilylethyl polydimethy siloxyethylhexyldimethicone[2)] | 37.5 |
| 7. | Aqueous dispersion obtained in Example 1. | 45.0 |
| 8. | Dipropylene glycol | 25.0 |
| 9. | Paraoxybenzoate methylester | 1.5 |
| 10. | Water | 53.5 |

[1)]Polyether modified silicone: KF-6017, manufactured by Shin-Etsu Chemical Co., Ltd.
[2)]Triethoxysilylethyl polydimethylsiloxyethylhexyl dimeticone: KF-9909, manufactured by Shin-Etsu Chemical Co., Ltd.

Preparation of a Foundation

The aforesaid components 1 to 4 were mixed, and the aforesaid components 5 and 6 were added thereto and mixed to be homogeneous. The aforesaid components 7 to 11 were mixed in a vessel and added to the mixture of the components 1 to 6 under stirring with a homomixer and emulsified to obtain a foundation.

Evaluation of the Foundation

The foundation obtained was transferred to a 500-milliliter plastic bottle and allowed to stand for one day and, then, a sensory test on odor was conducted. No odor was sensed.

Comparative Example 1

Example 1 was repeated to prepare an aqueous dispersion containing silicone elastomer particles, except that tocopherol was not used. The shape of the silicone elastomer particles in the aqueous dispersion thus obtained was spherical under observation with an optical microscope and the volume-average particle diameter thereof was 3 μm, as determined with a particle size distribution measurement instrument using an electric resistance method, Multisizer 3, manufactured by Beckman Coulter, Inc.

The aqueous dispersion obtained was transferred to a one-liter plastic bottle and allowed to stand for one day and, then, a sensory test on odor was conducted. Odor was sensed.

Comparative Example 2

Example 2 was repeated to prepare an aqueous dispersion containing silicone elastomer particles, except that tocopherol was not used. The shape of the silicone elastomer particles in the aqueous dispersion thus obtained was spherical under observation with an optical microscope and the volume-average particle diameter thereof was 12 μm, as determined with a particle size distribution measurement instrument using an electric resistance method, Multisizer 3, manufactured by Beckman Coulter, Inc.

Subsequently, the water was removed from the aqueous dispersion by volatilization in the same manner as in Example 2 to obtain silicone elastomer particles. The polyoxyethylene lauryl ether is non-volatile and, therefore, the entire amount of polyoxyethylene lauryl ether used adhered on the surface of the silicone elastomer particle. The shape of the silicone elastomer particles thus obtained was spherical under observation with an electron microscope.

The silicone elastomer particles obtained were transferred to a two-liter plastic bottle and allowed to stand for one day and, then, a sensory test on odor was conducted. No odor was sensed. Further, the silicone elastomer particle was stored at normal room temperature for one month and, then, a sensory test on odor was conducted. Odor was sensed.

Comparative Example 3

Foundation

Example 3 was repeated to prepare a foundation, except that the aqueous dispersion obtained in Comparative Example 1 was used in place of the aqueous dispersion obtained in Example 1. The foundation obtained was transferred to a 500-milliliter plastic bottle and allowed to stand for one day and, then, a sensory test on odor was conducted. Odor was sensed.

Comparative Example 4

Foundation

In a one-liter glass beaker, put were 457 g of methyl vinyl polysiloxane which is represented by the aforesaid formula (1) and has a dynamic viscosity of 130 mm$^2$/s and 43 g of a methyl hydrogen polysiloxane which is represented by the aforesaid formula (2) and has a dynamic viscosity of 30 mm$^2$/s, wherein this amount of the methyl hydrogen polysiloxane gives the number of the hydrosilyl groups of 1.17, per olefinically unsaturated group of the methyl vinyl polysiloxane, and stirred with a homomixer at 2,000 rpm to be dissolved each other.

Subsequently, 6 g of polyoxyethylene lauryl ether having 9 units derived from ethylene oxide, and 40 g of water were added and, then, stirred with a homomixer at 8,000 rpm, whereby an oil-in-water state was obtained and thickening was observed. Then, the stirring was continued for further 15 minutes.

Subsequently, 497 g of water was added thereto with stirring at 2,000 rpm to obtain a homogenous white emulsion. This emulsion was taken in a one-liter glass flask equipped with a stirrer having anchor type stirring blades, and the temperature was adjusted to 15-20 degrees C., to which then added with stirring was a solution consisting of 0.8 g of a solution of chloroplatinic acid-olefin complex in isododecane, containing 0.5 mass % of platinum, and 1 g of polyoxyethylene lauryl ether having 9 units derived from ethylene oxide. The resulting mixture was stirred for 12 hours at the same temperature.

Subsequently, 43 g of polyoxyethylene lauryl ether having 9 units derived from ethylene oxide, 5 g of sodium benzoate, 1 g of citric acid and 0.10 g of ascorbic acid were added to the resulting mixture and stirred for 10 minutes at the same temperature to obtain an aqueous dispersion which contains ascorbic acid in water. Ascorbic acid is water-soluble and insoluble in silicones. Accordingly, the silicone elastomer particles contained in the aqueous dispersion obtained in Comparative Example 4 did not contain ascorbic acid, i.e. antioxidant, and ascorbic acid was contained in water.

The shape of the silicone elastomer particles in the aqueous dispersion thus obtained was spherical under observation with an optical microscope and the volume-average particle diameter thereof was 3 μm, as determined with a particle size distribution measurement instrument using an electric resistance method, Multisizer 3, manufactured by Beckman Coulter, Inc.

Example 3 was repeated to prepare a foundation, excepted that the aqueous dispersion obtained in this Comparative Example 4 was used in place of the aqueous dispersion obtained in Example 1. The foundation obtained was transferred to a 500-milliliter plastic bottle and allowed to stand for one day and, then, a sensory test on odor was conducted. Odor was sensed.

Industrial Applicability

The present silicone elastomer particle and aqueous dispersion containing the silicone elastomer particle prevent oxygenation of nonionic surfactants and, therefore, generation of odor over time was prevented. Accordingly, the present silicone elastomer particle and aqueous dispersion are suitable for use in cosmetics.

The invention claimed is:

1. A method for preparing an aqueous dispersion comprising a nonionic surfactant, water, and a silicone elastomer particle having a crosslinking structure formed by an addition of a monovalent aliphatic unsaturated group bonded to a silicon atom and a hydrogen atom bonded to another silicon atom, wherein the silicone elastomer particle contains therein an antioxidant, the method comprising dissolving the antioxidant in a liquid silicone mixture comprising an organo(poly)siloxane having at least two monovalent aliphatic unsaturated groups each bonded to each one silicon atom and an organohydrogen(poly)siloxane having at least two hydrogen atoms each bonded to each one silicon atom, provided that the number of the monovalent aliphatic unsaturated groups each bonded to each one silicon atom in the organo(poly)siloxane is at least three and/or the number of the hydrogen atoms each bonded to each one silicon atom in the organohydrogen(poly)siloxane is at least three; subsequently adding water and the nonionic surfactant thereto, stirring and emulsifying them, and curing the mixture in the presence of a platinum group metal catalyst.

2. The method according to claim 1, wherein the antioxidant is soluble in a liquid silicone.

3. The method according to claim 1, wherein the antioxidant is insoluble in water.

4. The method according to claim 1, wherein the antioxidant is one or more selected from the group consisting of tocopherol, p-t-butylphenol, butylhydroxyanisol, dibutylhydroxytoluene, pentaerythritol tetrakis(3,5-di-tert-butyl-4-hydroxyhydrocinnamate) and ethoxyquin.

5. The method according to claim 1, wherein an amount of the antioxidant is an effective amount so as to prevent oxygenation of the nonionic surfactant.

6. A method for preparing an aqueous dispersion comprising a nonionic surfactant, water, and a silicon elastomer particle having a crosslinking structure formed by an addition reaction of a monovalent aliphatic unsaturated group bonded to a silicon atom and a hydrogen atom bonded to another silicon atom, wherein the silicone elastomer particle contains therein an antioxidant, the method comprising stirring water, the nonionic surfactant and a liquid silicone mixture comprising an organo(poly)siloxane having at least two monovalent aliphatic unsaturated groups each bonded to each one silicon atom and an organohydrogen(poly)siloxane having at least two hydrogen atoms each bonded to each one silicon atom, provided that the number of the monovalent aliphatic unsaturated groups each bonded to each one silicon atom in the organo(poly)siloxane is at least three and/or the number of the hydrogen atoms each bonded to each one silicon atom in the organohydrogen(poly)siloxane is at least three to emulsify them; subsequently adding an antioxidant which is soluble in the liquid silicone mixture and insoluble in water with stirring; and, then, curing the mixture in the presence of a platinum group metal catalyst.

7. The method according to claim 6, wherein the antioxidant is one or more selected from the group consisting of tocopherol, p-t-butylphenol, butylhydroxyanisol, dibutylhydroxytoluene, pentaerythritol tetrakis(3,5-di-tert-butyl-4-hydroxyhydrocinnamate) and ethoxyquin.

8. The method according to claim 6, wherein an amount of the antioxidant is an effective amount so as to prevent oxygenation of the nonionic surfactant.

9. A method for preparing the silicone elastomer particle having crosslinking structure formed by an addition reaction of a monovalent aliphatic unsaturated group bonded to a silicon atom and a hydrogen atom bonded to another silicon atom, wherein the silicone elastomer particle contains therein an antioxidant, comprising removing water from an aqueous dispersion obtained in a method comprising dissolving an antioxidant in a liquid silicone mixture comprising an organo(poly)siloxane having at least two monovalent aliphatic unsaturated groups each bonded to each one silicon atom and an organohydrogen(poly)siloxane having at least two hydrogen atoms each bonded to each one silicon atom, provided that the number of the monovalent aliphatic unsaturated groups each bonded to each one silicon atom in the organo(poly)siloxane is at least three and/or the number of the hydrogen atoms each bonded to each one silicon atom in the organohydrogen(poly)siloxane is at least three; subsequently adding water and a nonionic surfactant thereto, stirring and emulsifying them, and curing the mixture in the presence of a platinum group metal catalyst to obtain a silicone elastomer particle.

10. The method according to claim 9, wherein an amount of the antioxidant is an effective amount so as to prevent oxygenation of the nonionic surfactant.

11. A method for preparing a silicone elastomer particle having a crosslinking structure formed by an addition reaction of a monovalent aliphatic unsaturated group bonded to a silicon atom and a hydrogen atom bonded to another silicon atom, wherein the silicone elastomer particle contains therein an antioxidant, comprising removing water from an aqueous dispersion obtained in a method comprising stirring water, a nonionic surfactant and a liquid silicone mixture comprising an organo(poly)siloxane having at least two monovalent aliphatic unsaturated groups each bonded to each one silicon atom and an organohydrogen(poly)siloxane having at least two hydrogen atoms each bonded to each one silicon atom, provided that the number of the monovalent aliphatic unsaturated groups each bonded to each one silicon atom in the organo(poly)siloxane is at least three and/or the number of the hydrogen atoms each bonded to each one silicon atom in the organohydrogen(poly)siloxane is at least three to emulsify them; subsequently adding the antioxidant that is soluble in the liquid silicone mixture and insoluble in water with stirring; and, then, curing the mixture in the presence of a platinum group metal catalyst to obtain the silicone elastomer particle.

12. The method according to claim 11, wherein an amount of the antioxidant is an effective amount so as to prevent oxygenation of the nonionic surfactant.

* * * * *